(12) United States Patent
Li et al.

(10) Patent No.: US 7,696,241 B2
(45) Date of Patent: Apr. 13, 2010

(54) BICYCLIC COMPOUNDS AS MODULATORS OF ANDROGEN RECEPTOR FUNCTION AND METHOD

(75) Inventors: James J. Li, Pennington, NJ (US); Lawrence Hamann, Cherry Hill, NJ (US); Haixia Wang, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 349 days.

(21) Appl. No.: 11/070,025

(22) Filed: Mar. 2, 2005

(65) Prior Publication Data

US 2007/0004717 A1    Jan. 4, 2007

Related U.S. Application Data

(60) Provisional application No. 60/550,155, filed on Mar. 4, 2004.

(51) Int. Cl.
*A61K 31/403* (2006.01)
*C07D 209/52* (2006.01)

(52) U.S. Cl. ....................... 514/421; 548/512
(58) Field of Classification Search ................ 514/421; 548/512, 515
See application file for complete search history.

(56) References Cited

U.S. PATENT DOCUMENTS

| | | | |
|---|---|---|---|
| 3,239,345 A | 3/1966 | Hodge et al. | |
| 3,948,933 A | 4/1976 | Fontanella | |
| 4,036,979 A | 7/1977 | Asato | |
| 4,411,890 A | 10/1983 | Momany et al. | |
| 4,959,361 A | 9/1990 | Walser et al. | |
| 5,179,080 A | 1/1993 | Rothkopf et al. | |
| 5,403,817 A | 4/1995 | Seckinger et al. | |
| 5,482,921 A | 1/1996 | Seckinger et al. | |
| 5,488,064 A | 1/1996 | Sher | |
| 5,491,134 A | 2/1996 | Sher et al. | |
| 5,541,204 A | 7/1996 | Sher et al. | |
| 5,556,909 A | 9/1996 | Desai | |
| 5,605,877 A | 2/1997 | Schafer et al. | |
| 5,612,359 A | 3/1997 | Merugesan et al. | |
| 5,688,808 A | 11/1997 | Jones et al. | |
| 5,688,810 A | 11/1997 | Jones et al. | |
| 5,693,646 A | 12/1997 | Jones et al. | |
| 5,693,647 A | 12/1997 | Jones et al. | |
| 5,696,127 A | 12/1997 | Jones et al. | |
| 5,696,130 A | 12/1997 | Jones et al. | |
| 5,696,133 A | 12/1997 | Jones et al. | |
| 5,770,615 A | 6/1998 | Cheng et al. | |
| 5,776,983 A | 7/1998 | Washburn et al. | |
| 5,811,374 A | 9/1998 | Bertram et al. | |
| 6,011,029 A | 1/2000 | Ding et al. | |
| 6,040,321 A | 3/2000 | Kim et al. | |
| 6,043,265 A | 3/2000 | Merugusan et al. | |
| 6,184,231 B1 | 2/2001 | Hewawasam et al. | |
| 6,310,095 B1 | 10/2001 | Sebti et al. | |
| 6,365,615 B1 | 4/2002 | Kelly et al. | |
| 6,531,612 B2 | 3/2003 | Gabriel et al. | |
| 6,566,367 B2 | 5/2003 | Bakthavatchalam et al. | |
| 6,670,386 B2 | 12/2003 | Sun et al. | |
| 6,710,064 B2 | 3/2004 | Launay et al. | |
| 6,897,225 B1 | 5/2005 | Sircar et al. | |
| 6,974,823 B2 | 12/2005 | Hamilton et al. | |
| 2004/0019063 A1 | 1/2004 | Sun et al. | |
| 2004/0181064 A1 | 9/2004 | Sun et al. | |
| 2005/0059652 A1 | 3/2005 | Hamann et al. | |

FOREIGN PATENT DOCUMENTS

| | | |
|---|---|---|
| AU | A-82875/87 | 6/1988 |
| DE | 2126187 | 5/1971 |
| DE | 3809390 | 9/1989 |
| EP | 0272594 | 6/1988 |
| EP | 0493323 | 7/1992 |
| EP | 1004583 | 5/2000 |
| EP | 1125925 | 8/2001 |
| GB | 1503244 | 3/1978 |
| JP | 52 083686 | 7/1977 |
| WO | WO89/07110 | 8/1989 |
| WO | WO 89/07111 | 8/1989 |
| WO | WO 93/04081 | 3/1993 |
| WO | WO 94/14817 | 7/1994 |
| WO | WO 96/19458 | 6/1996 |
| WO | WO 97/19086 | 5/1997 |
| WO | WO 97/21993 | 6/1997 |

(Continued)

OTHER PUBLICATIONS

Matsuki et al., Chem. Pharm. Bull. 42(1), p. 9-18 (1994).*

(Continued)

*Primary Examiner*—Yong Chu
*Assistant Examiner*—Joseph K McKane
(74) *Attorney, Agent, or Firm*—Maureen S. Gibbons; Burton Rodney

(57) ABSTRACT

The present invention relates to bicyclic compounds according to formula I, pharmaceutical compositions containing such compounds and methods of using such compounds in the treatment of androgen receptor-associated conditions, such as age-related diseases, for example sarcopenia,

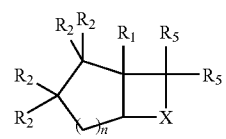

wherein $R_1$, $R_2$, $R_5$, X and n are defined herein.

7 Claims, No Drawings

FOREIGN PATENT DOCUMENTS

| WO | WO 97/30992 | 8/1997 |
|---|---|---|
| WO | WO 97/49709 | 12/1997 |
| WO | WO 98/22461 | 5/1998 |
| WO | WO 98/25929 | 6/1998 |
| WO | WO 98/38192 | 9/1998 |
| WO | WO 98/54966 | 12/1998 |
| WO | WO 99/00353 | 1/1999 |
| WO | WO 99/01124 | 1/1999 |
| WO | WO 99/02224 | 1/1999 |
| WO | WO 99/02514 | 1/1999 |
| WO | WO 99/03848 | 1/1999 |
| WO | WO 99/07692 | 2/1999 |
| WO | WO 99/24416 | 5/1999 |
| WO | WO 99/27890 | 6/1999 |
| WO | WO 99/28324 | 6/1999 |
| WO | WO 99/43653 | 9/1999 |
| WO | WO 99/54318 | 10/1999 |
| WO | WO 99/54319 | 10/1999 |
| WO | WO 99/54330 | 10/1999 |
| WO | WO 99/65913 | 12/1999 |
| WO | WO 99/67252 | 12/1999 |
| WO | WO 99/67253 | 12/1999 |
| WO | WO 00/00485 | 1/2000 |
| WO | WO 00/01389 | 1/2000 |
| WO | WO 00/13508 | 3/2000 |
| WO | WO 00/59874 | 10/2000 |
| WO | WO 00/72845 | 12/2000 |
| WO | WO 01/16108 | 3/2001 |
| WO | WO 01/16133 | 3/2001 |
| WO | WO 01/16139 | 3/2001 |
| WO | WO 01/30781 | 5/2001 |
| WO | WO 01/46195 | 6/2001 |
| WO | WO 01/54498 | 8/2001 |
| WO | WO 01/70684 | 9/2001 |
| WO | WO0170684 | 9/2001 |
| WO | WO0172705 | 10/2001 |
| WO | WO0200653 | 1/2002 |
| WO | WO 01/07052 | 2/2002 |
| WO | WO0218335 | 3/2002 |
| WO | WO03011824 | 2/2003 |
| WO | WO03066636 | 8/2003 |
| WO | WO 94/05668 | 3/2004 |

OTHER PUBLICATIONS

U.S. Appl. No. 10/984,502, filed Nov. 9, 2004, Bi et al.
U.S. Appl. No. 11/048,437, filed Feb. 1, 2005, Nirschl et al.
U.S. Appl. No. 11/048,439, filed Feb. 1, 2005, Hamann et al.
U.S. Appl. No. 11/070,020, filed Mar. 2, 2005, Li et al.
U.S. Appl. No. 11/070,808, filed Mar. 2, 2005, Nirschl et al.
Banz, W.J. et al., "Effects of Soy Protein and Soy Phytoestrogens on Symptoms Associated with Cardiovascular Disease in Rats", Journal of Medicinal Food, vol. 2, Nos. 3-4, pp. 271-273 (1999).
Boeijen, A. et al., "Combinatorial Chemistry of Hydantoins", Bioorganic & Medicinal Chemistry Letters, vol. 8, pp. 2375-2380 (1998).
Bourguet, W. et al., "Crystal structure of the ligand-binding domain of the human nuclear receptor RXR-α", Nature, vol. 375, pp. 377-382 (1995).
Brzozowski, A.M. et al., "Molecular basis of agonism and antagonism in the oestrogen receptor", Nature, vol. 389, pp. 753-758 (1997).
Evans, R.M., "The Steroid and Thyroid Hormone Receptor Superfamily", Science, vol. 240, pp. 889-895 (1988).
Grese, T.A. et al., "Molecular determinants of tissue selectivity in estrogen receptor modulators", Proc. Natl. Acad. Sci. USA, vol. 94, pp. 14105-14110 (1997).
Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", J. Med. Chem., vol. 42, No. 2, pp. 210-212 (1999).

Hamann, L.G. et al., "Synthesis and Biological Activity of a Novel Series of Nonsteroidal, Peripherally Selective Androgen Receptor Antagonists Derived from 1,2-Dihydropyridono[5,6-g]quinolines", J. Med. Chem., vol. 41, No. 4, pp. 623-639 (1998).
Hempstock, J. et al., "Growth inhibition of prostate cell lines in vitro by phyto-oestrogens", British Journal of Urology, vol. 82, pp. 560-563 (1998).
Neri, R. et al., "A Biological Profile of a Nonsteroidal Antiandrogen, SCH 13521 (4'-Nitro-3'-Trifluoromethylisobutyranilide)", Endocrinology, vol. 91, No. 2, pp. 427-437 (1972).
Quella, S.K. et al., "Evaluation of Soy Phytoestrogens for the Treatment of Hot Flashes in Breast Cancer Survivors: A North Central Cancer Treatment Group Trial", Journal of Clinical Oncology, vol. 18, No. 5, pp. 1068-1074 (2000).
Regal, J.F. et al., "Dietary Phytoestrogens Have Anti-Inflammatory Activity in a Guinea Pig Model of Asthma", Proc. Soc. Exp. Biol. Med., vol. 223, pp. 372-378 (2000).
Shiau, A.K. et al., "The Structural Basis of Estrogen Receptor/Coactivator Recognition and the Antagonism of This Interaction by Tamoxifen", Cell, vol. 95, pp. 927-937 (1998).
Smigel, K., "Breast Cancer Prevention Trial Shows Major Benefit, Some Risk", Journal of the National Cancer Institute, vol. 90, No. 9, pp. 647-648 (1998).
Tanenbaum, D.M. et al., "Crystallographic comparison of the estrogen and progesterone receptor's ligand binding domains", Proc. Natl. Acad. Sci. USA, vol. 95, pp. 5998-6003 (1998).
Vegeto, E. et al., "The Mechanism of RU486 Antagonism Is Dependent on the Conformation of the Carboxy-Terminal Tail of the Human Progesterone Receptor", Cell, vol. 69, pp. 703-713 (1992).
Banker et al., "Modern Pharmaceuticals, 3rd ed.", Marcel Dekker, New York, 1996, pp. 451 and 596.
Beyler et al., J. Am. Med. W. Assoc., 23(8): 708-721.
Boris et al., Steroids, 15:61-71.
Bundgaard, "Design of Prodrugs", Elsevier Science Publishers 1985, table of contents.
Bundgaard, "Design and Application of Prodrugs", Harwood Academic Publishers 1991, pp. 113-191.
Chalepakis et al., Cell, 53: 371-382.
Delaisi et al., J. Steroid Biochem. Molec. Biol. 41(3-8) 773-7.
Dyatkin Tet Lett 38(12): 2065-6.
Edwards et al., Bioorg. Med. Chem. Lett 9:1003-8.
Fernand Labrie, Int'l Braz. J. Urol. 30(1):3-11.
Gori et al., Boll.-Soc. Ital. Boil. Sper. 42:1596-1599.
Gori et al., Boll.-Soc. Ital. Boil. Sper. 42:1600-1601.
Heiser, in Methods in Mol. Biol. 130: 117-134.
Hempstock et al., J. Med. Food 2(3-4): 243-246.
Hershberger et al.; P.S.E.B.M. 83:175-180.
Hiroaka et al., Cancer Res., 47:6560-6564.
Imakura et al., Chem. Pharm. Bull. 40(7): 1691-1696.
Iseki, K. et al., Tet. 53(10) 3513-26.
Issartel et al., 1996, CAS 125:316198.
Johannsson et al., J. Clin. Endocr. Met. 82(3): 727-734.
Kakigami et al., Chem. Pharm. Bull. 46(1):42-52.
Lalezari et al., J. Het Chem. 20(2) 483-485 (1983).
Milata et al., Org. Prep. Proc. Int'l, 25(6): 703-704.
Minesita et al., Cancer Research 25:1168-1175.
Montes de Oca et al., Arkivoc, 390-403 (2003).
Navone et al., Clin. Canc. Res. 3:2493-2500.
Okuda et al., J. Urology 145: 188-191.
Palovich et al., 2000, CAS 134:25357.
Panouse et al., Ann. Pharm. Franc., 2000- 291-302.
Rodbard in Ligand Assay, Masson Publishing USA Inc., 1981, pp. 45-101.
Schuur et al., J. Biol. Chem. 271(12): 7043-7051.
Suzuki et al., J. Steroid Chem. Mol. Biol. 37(4): 559-567.
Talon et al., Br. J. Pharmacol., 134(7): 1523-31.
Taplin et al., J. Cell Biochem. 91 (3):483-490.
Uozumi, Tet Lett 42:407-410.
Uozumi, Tet Lett 42:411-414.
Venable, Am. J. Anat. 119: 263-270.
Wermuth et al. in The Practice of Medicinal Chemistry, Academic Press, 1996, pp. 671-696.

Wolft "Burger's Medicinal Chemistry, 5th ed. Part 1", John Wily & Sons 1995, pp. 975-977.

Klapars, et al., "A General and Efficient Copper Catalyst for the Amidation of Aryl Halides and the N-Arylation of Nitrogen Heterocycles," *Journal of the American Chemical Society*, vol. 123, No. 31, pp. 7727-7729 (2001).

\* cited by examiner

BICYCLIC COMPOUNDS AS MODULATORS OF ANDROGEN RECEPTOR FUNCTION AND METHOD

RELATED APPLICATIONS

This application claims priority benefit under Title 35 § 119(e) of U.S. provisional Application No. 60/550,155, filed Mar. 4, 2004, the contents of which are herein incorporated by reference.

FIELD OF THE INVENTION

The present invention relates to bicyclic compounds, methods of using such compounds in the treatment of androgen receptor-associated conditions, such as age-related diseases, for example sarcopenia, to pharmaceutical compositions containing such compounds.

BACKGROUND OF THE INVENTION

Nuclear hormone receptors (NHR's) constitute a large super-family of structurally-related and sequence-specific gene regulators scientists have named "ligand-dependent transcription factors." R. M. Evans, *Science*, 240:889 (1988). The steroid binding NHR's (SB-NHR's) form a recognized subset of the NHR's, including the progesterone receptor (PR), androgen receptor (AR), estrogen receptor (ER), glucocorticoid receptor (GR) and mineralocorticoid receptor (MR). The conventional nuclear hormone receptors are generally transactivators in the presence of ligand, which selectively bind to the NHR in a way that effects gene transcription. In the absence of a corresponding ligand, some of the orphan receptors behave as if they are transcriptionally inert. Others, however, behave as either constitutive activators or repressors. These orphan nuclear hormone receptors are either under the control of ubiquitous ligands that have not been identified, or do not need to bind ligand to exert these activities.

The AR is a ligand-activated transcriptional regulatory protein that mediates induction of male sexual development and function through its activity with endogenous androgens. In addition, androgens are associated with male and female maintenance of muscle mass and strength, bone mass and erythropoiesis. Androgens, such as testosterone, also play an important role in many physiological processes, such as differentiation of male internal and external genitalia, development and maintenance of male secondary sexual characteristics (e.g., the development of prostate, seminal vesicles, penis, scrotum, skeletal muscle, redistribution of body fat, stimulation of long bone growth, closure of epiphyses, development of male hair growth pattern and enlargement of larynx), the maintenance of sexual behavior and function (e.g., libido and potency) and spermatogenesis (in man).

As one ages, the serum androgen concentration in the body declines. The age dependent decline in androgens is associated with changes in body composition for men and women, such as a lower percentage of muscle mass and an increase in body fat, e.g., sarcopenia. In this regard, modulation of the AR gene can have an impact on the physiological effects associated with androgen production. However, the effectiveness of known modulators of steroid receptors is often tempered by their undesired side-effect profile, particularly during long-term administration. For example, the administration of synthetic androgens has been associated with liver damage, prostate cancer, adverse effects on male sexual function and adverse effects associated with cardiovascular and erythropoietic function.

Numerous synthetically-derived steroidal and non-steroidal agonists and antagonists have been described for the members of the SB-NHR family. Many of these agonist and antagonist ligands are used clinically in man to treat a variety of medical conditions. RU486 (mifepristone) is an example of a synthetic antagonist of the PR, which is utilized as a birth control agent (Vegeto et al., *Cell* 69: 703-713 (1992)). Flutamide is an example of an antagonist of the AR, which is utilized for the treatment of prostate cancer (Neri et al, *Endo*. 91, 427-437 (1972)). Tamoxifen is an example of a tissue-selective modulator of the ER function, that is used in the treatment of breast cancer (Smigel *J. Natl. Cancer Inst*. 90, 647-648 (1998)). Tamoxifen can function as an antagonist of the ER in breast tissue while acting as an agonist of the ER in bone (Grese et al., *Proc. Natl. Acad. Sci. USA* 94, 14105-14110 (1997)). Because of the tissue-selective effects seen for Tamoxifen, this agent, and agents like it, are referred to as tissue-selective estrogen receptor modulators. In addition to synthetically-derived non-endogenous ligands, non-endogenous ligands for NHR's can be obtained from food sources (Regal et al., *Proc. Soc. Exp. Biol. Med*. 223, 372-378 (2000) and Hempstock et al., *J. Med. Food* 2, 267-269 (1999)). The flavanoid phytoestrogens are an example of an unnatural ligand for SB-NHR's that are readily obtained from a food source such as soy (Quella et al., *J. Clin. Oncol*. 18, 1068-1074 (2000) and Banz et al., *J. Med. Food* 2, 271-273 (1999)). The ability to modulate the transcriptional activity of an individual NHR by the addition of a small molecule ligand, makes these receptors ideal targets for the development of pharmaceutical agents for a variety of disease states.

As mentioned above, non-natural ligands can be synthetically engineered to serve as modulators of the function of NHR's. In the case of SB-NHR's, engineering of an unnatural ligand can include the identification of a core structure which mimics the natural steroid core system. This can be achieved by random screening against several SB-NHR's, or through directed approaches using the available crystal structures of a variety of NHR ligand binding domains (Bourguet et al., *Nature* 375, 377-382 (1995), Brzozowski, et al., *Nature* 389, 753-758 (1997), Shiau et al., *Cell* 95, 927-937 (1998) and Tanenbaum et al., *Proc. Natl. Acad. Sci. USA* 95, 5998-6003 (1998)). Differential substitution about such a steroid mimic core can provide agents with selectivity for one receptor versus another. In addition, such modifications can be employed to obtain agents with agonist or antagonist activity for a particular SB-NHR. Differential substitution about the steroid mimic core can result in the formation of a series of high affinity agonists and antagonists with specificity for, for example, ER versus PR versus AR versus GR versus MR. Such an approach of differential substitution has been reported, for example, for quinoline based modulators of steroid NHRs in Hamann et. al., *J. Med. Chem.*, 41, 623 (1998); Hamann et. al., *J. Med. Chem.* 42, 210 (1999); WO 9749709; U.S. Pat. No. 5,696,133; U.S. Pat. No. 5,696,130; U.S. Pat. No. 5,696,127; U.S. Pat. No. 5,693,647; U.S. Pat. No. 5,693,646; U.S. Pat. No. 5,688,810; U.S. Pat. No. 5,688,808 and WO 9619458, all incorporated herein by reference.

Accordingly, identification of compounds which have good specificity for one or more steroid receptors, but which have reduced or no cross-reactivity for other steroid or intracellular receptors, would be of significant value in the treatment of male and female hormone-responsive diseases. There is, therefore, a need in the art for the identification of selective modulators of the steroid binding nuclear hormone receptors, particularly non-steroidal, non-toxic tissue selective androgen receptor modulators, which activate the androgen receptor in skeletal muscle while demonstrating limited or neutral effect on other androgen responsive (e.g., prostate) tissues.

SUMMARY OF THE INVENTION

In a first embodiment of the present invention, compounds are provided which are capable of modulating the function of a nuclear hormone receptor having the general formula I:

I wherein $R_1$ is independently selected from the group consisting of H, alkyl, substituted alkyl, alkenyl, substituted alkenyl, arylalkyl, substituted arylalkyl, $CO_2R_4$, $CONR_4R_4$, and $CH_2OR_4$;

$R_2$ is independently selected from the group consisting of H, alkyl, substituted alkyl, $OR_3$, $SR_3$, halo, $NHR_3$, $NHCOR_4$, $NHCO_2R_4$, $NHCONR_4R_4$ and $NHSO_2R_4$;

$R_3$ is independently selected from the group consisting of H, alkyl, substituted alkyl, $CHF_2$, $CF_3$ and $COR_4$;

$R_4$, is independently selected from the group consisting of H, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;

$R_5$ is independently selected from the group consisting of H, $CF_3$, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;

$R_6$ is selected from the group consisting of G and $CH_2G$;

G is selected from the group consisting of aryl, heterocyclo and heteroaryl, wherein said aryl, heterocyclo or heteroaryl is mono- or polycyclic, and is optionally substituted with one or more substituents selected from the group consisting of hydrogen, halo, CN, $CF_3$, $OR_4$, $CO_2R_4$, $NR_4R_4$, $CONR_4R_4$, $CH_2OR_4$, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl; and n is 1 or 2; wherein the definition of formula I above includes all prodrug esters, stereoisomers and pharmaceutically acceptable salts of formula I.

A preferred embodiment of the present invention provides compounds of formula I wherein $R_1$ is H or alkyl;

$R_2$ is OH;

$R_5$ is alkyl or substituted alkyl;

X is (where N is attached to the carbon atom bearing the $R_5$ substituents); and n is 1.

A further preferred embodiment includes compounds of formula I where G is selected from:

wherein $R_8$, $R_9$, $R_{10}$ and $R_{11}$ are independently selected from the group consisting of H, $NO_2$, CN, $CF_3$, $OR_4$, $CO_2R_4$, $NR_4R_4$, $CONR_4R_4$, $CH_2OR_4$, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;

A, B, C, D, E and F are independently selected from the group consisting of N and $CR_{12}$;

J, K, L, P and Q are independently selected from the group consisting of $NR_{13}$, O, S, SO, $SO_2$ and $CR_{13}R_{13}$;

$R_{12}$ is independently selected from the group consisting of a direct bond and $R_{13}$;

$R_{13}$ is independently selected from the group consisting of H, alkyl, substituted alkyl, alkenyl, substituted alkenyl, arylalkyl, substituted arylalkyl, $CO_2R_4$, $CONR_4R_4$ and $CH_2OR_4$; and z is 0 or 1.

A still further preferred embodiment of the present invention provides compounds wherein $R_8$ is CN.

The compounds of formula I modulate the function of the nuclear hormone receptors, particularly the androgen receptor, and include compounds which are, for example, selective agonists, partial agonists, antagonists or partial antagonists of the androgen receptor. Preferably the compounds of formula I possess activity as agonists of the androgen receptor and may be used in the treatment of diseases or disorders associated with androgen receptor activity, such as maintenance of muscle strength and function (e.g., in the elderly); reversal or prevention of frailty or age-related functional decline ("ARFD") in the elderly (e.g., sarcopenia); prevention of catabolic side effects of glucocorticoids; prevention and treatment of reduced bone density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); treatment of urinary incontinence, acceleration of wound healing; accelerating bone fracture repair (such as accelerating the recovery of hip fracture patients); treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy.

In a second embodiment of the present invention, pharmaceutical compositions, comprising at least one compound according to formula I and at least one pharmaceutically acceptable diluent or carrier are provided.

In a third embodiment of the present invention, methods for preventing, inhibiting or treating the progression or onset of diseases or disorders associated with nuclear hormone receptors, comprising administering to a patient in need a theapeutically effective amount of a compound according to formula I are provided.

In a preferred embodiment of the present invention, methods are provided, wherein the nuclear hormone receptor is the androgen receptor.

In a further preferred embodiment of the present invention, methods are provided wherein the disease or disorder associated with the androgen receptor is selected from the group consisting of maintenance of muscle strength and function; reversal or prevention of frailty or age-related functional decline ("ARFD") in the elderly (e.g., sarcopenia); prevention of catabolic side effects of glucocorticoids; prevention and treatment of reduced bone density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); treatment of urinary incontinence, acceleration of wound healing; accelerating bone fracture repair (such as accelerating the recovery of hip fracture patients); treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy.

In a still further preferred embodiment of the present invention, methods further comprising a therapeutically effective amount of at least one other therapeutic agent are provided.

DETAILED DESCRIPTION OF THE INVENTION

Abbreviations
The following abbreviations are employed herein:
Chiralpak®=Trademark of Chiral Technologies, Inc. Eaton, Pa.
AcOH=acetic acid
DBU=1,8-diazabicyclo[5.4.0]undec-7-ene
EtOAc=ethyl acetate
HPLC=high performance liquid chromatography
MeOH=methanol
MS or Mass Spec=mass spectrometry
YMC®=trademark of YMC Co, Ltd., Kyoto, Japan
$CH_2Cl_2$=dichloromethane
CuBr=copper(I) bromide
CuI=copper(I) iodide
CuCN=copper(I) cyanide
DMF=N,N-dimethylforamide
$Et_3N$=triethylamine
LDA=lithium diisopropylamide
KOH=potassium hydroxide
$NaBH_4$=sodium borohydride
$Na_2SO_4$=sodium sulfate
Pd/C=palladium on activated charcoal
TFA=trifluoroacetic acid
THF=tetrahydrofuran
mp.=melting point
min=minute(s)
h=hour(s)
L=liter
mL=milliliter
µL=microliter
g=gram(s)
mg=milligram(s)
mol=moles
mmol=millimole(s)
nM=nanomolar
RT=room temperature Definitions The following definitions apply to the terms as used throughout this specification, unless otherwise limited in specific instances.

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

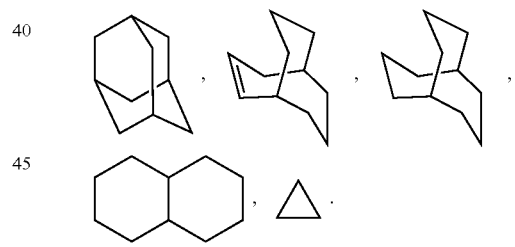

"Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The term "halogen" or "halo" as used herein alone or as part of another group refers to chlorine, bromine, fluorine, and iodine.

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings), for example "Substituted aryl" includes an aryl group optionally substituted with one or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Examples of heteroaryl groups include the following:

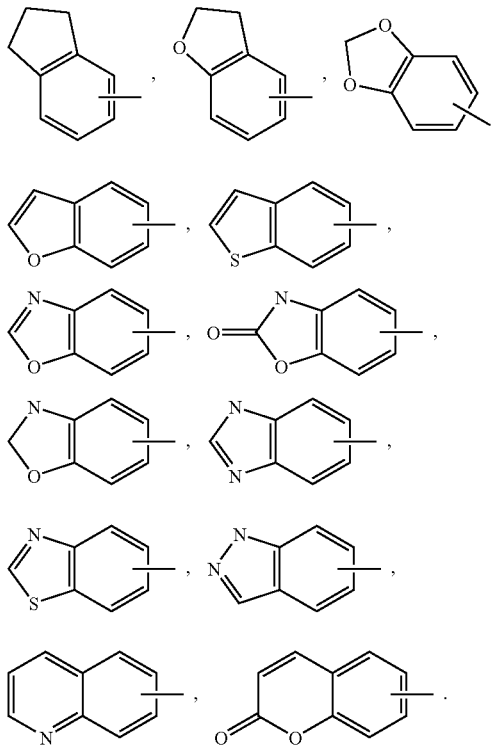

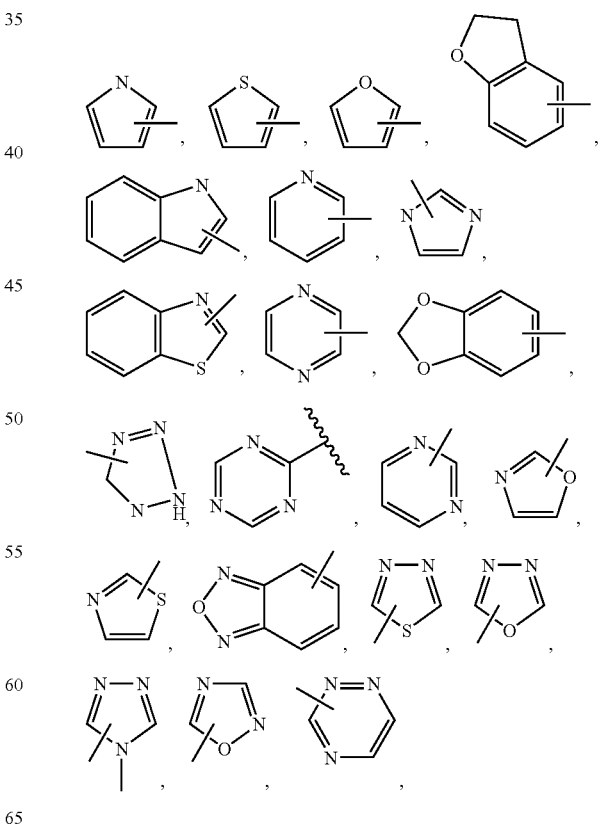

and the like.

The term "heterocyclo", heterocycle or heterocyclic ring, as used herein, represents an unsubstituted or substituted stable 5- to 7-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

(a) *The Practice of Medicinal Chemistry*, Camille G. Wermuth et al., Ch 31, (Academic Press, 1996);

(b) *Design of Prodrugs*, edited by H. Bundgaard, (Elsevier, 1985);

(c) *A Textbook of Drug Design and Development*, P. Krogsgaard-Larson and H. Bundgaard, eds., Ch. 5, pgs, 113-191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic, chiral HPLC or fractional crystallization.

The compounds of formula I of the present invention can be prepared as shown in the following reaction schemes and description thereof, as well as relevant published literature procedures that may be used by one skilled in the art. Exemplary reagents and procedures for these reactions appear hereinafter and in the working Examples.

Chemistry used to synthesize preferred compounds of the general structure I is shown below in Scheme I-III. Additional schemes will be added to enable the entire breadth of the genus.

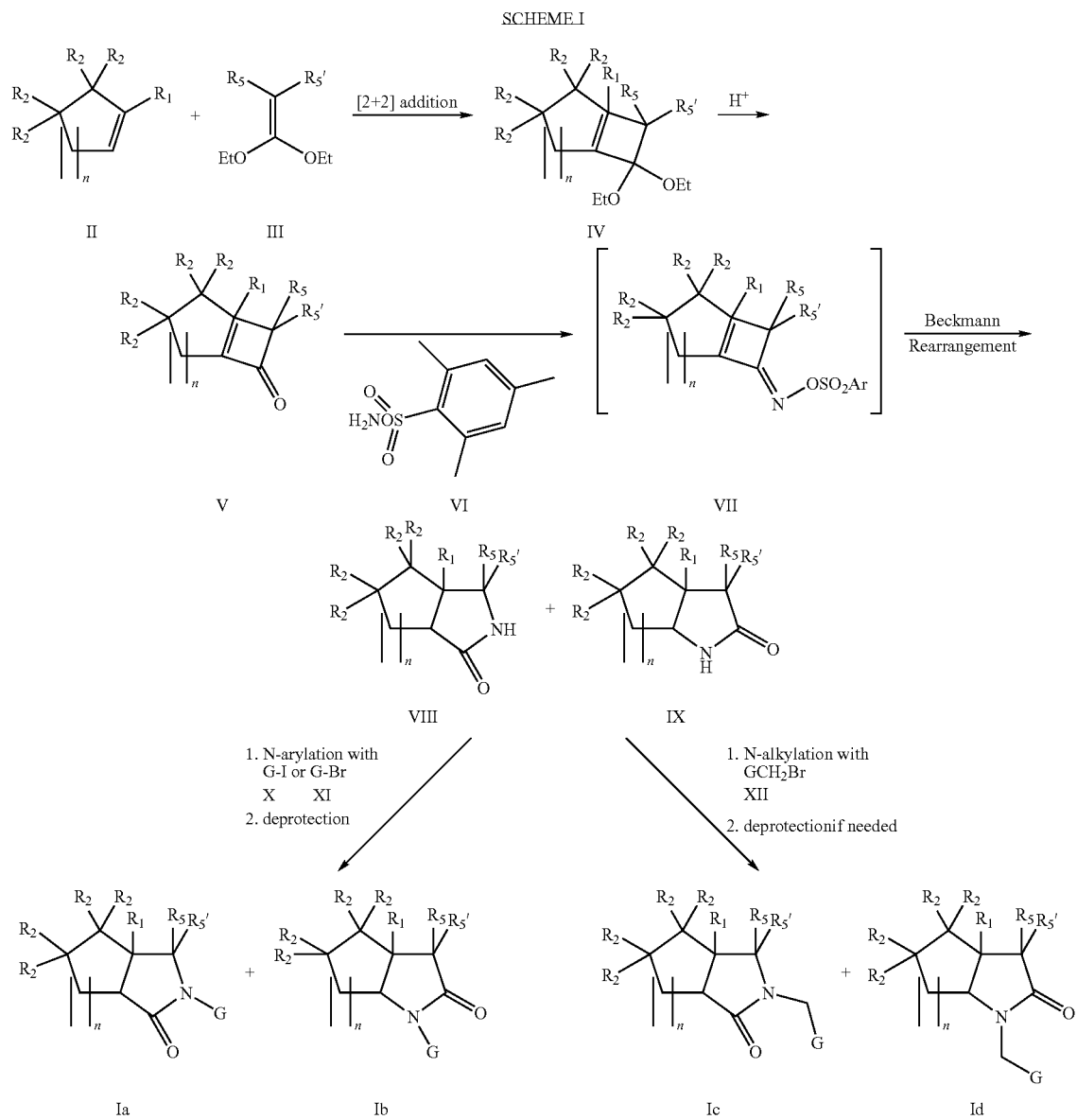

Scheme I describes methods for preparing compounds of formula I (subset structures as compounds Ia, Ib, Ic and Id). Photo-mediated [2+2] cycloaddition of compound II and III provide the adduct IV. Hydrolysis of ketal moiety under acid condition provide ketone intermediate V. In some cases, $R_2$ group in compound V can be protected by a suitable protecting group before next step.

Treatment of compound V with O-mesitylenesulfonyl-hydroxylamine VI give an oxime derivative VII which undergo a Bechmann Rearrangement to provide compounds VIII and IX. Cu or Pd catalyzed N-arylation of compounds VIII and IX with compound X or XI followed by deprotection step in $R_2$ (if needed) provide compounds Ia and Ib, respectively. Alkylation of compounds VIII and IX with compound XII followed by deprotection in $R_2$ (if needed) provide compounds Ic and Id, respectively.

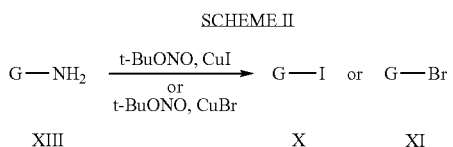

Scheme II describes a method to prepare compounds of formula X and XI. Intermediates XIII are treated with tert-butylnitrite or an equivalent reagent in the presence of a halide source such as CuI or CuBr to afford an aryl or heteroaryl halide of formula X or XI. Additional methods for preparing compounds X and XI can also be found in the literature or be readily carried out by one skilled in the art.

SCHEME III

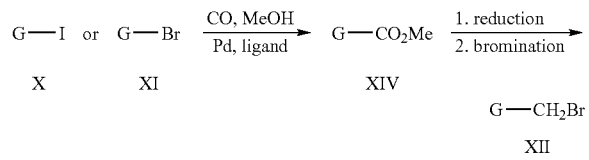

Scheme III describes a method to prepare compounds of formula XII. Carbonylation of either X or XI give an ester XIV. Sodium borohydride reduction of compound XIV followed by bromination with PBr$_3$ could provide compound XII. Additional methods for preparing compounds XII can also be found in the literature or be readily carried out by one skilled in the art.

Use and Utility

A. Utilities

The compounds of the present invention modulate the function of the nuclear hormone receptors, particularly the androgen receptor, and include compounds which are, for example, selective agonists, partial agonists, antagonists or partial antagonists of the androgen receptor (AR). Thus, the present compounds are useful in the treatment of AR-associated conditions. An "AR-associated condition," as used herein, denotes a condition or disorder which can be treated by modulating the function or activity of an AR in a subject, wherein treatment comprises prevention, partial alleviation or cure of the condition or disorder. Modulation may occur locally, for example, within certain tissues of the subject, or more extensively throughout a subject being treated for such a condition or disorder.

The compounds of the present invention can be administered to animals, preferably humans, for the treatment of a variety of conditions and disorders, including, but not limited to maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; conteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), urinary incontinence, male and female contraception, hair loss, Reaven's Syndrome and the enhancement of bone and muscle performance/strength. The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antibiotic or other pharmaceutically active material.

The compounds of the present invention may be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention may also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotonin 5-$HT_D$agonists, such as sumatriptan, or agents which inhibit somatostatin or its release, such as physostigmine and pyridostigmine. A still further use of the disclosed compounds of the invention is in combination with parathyroid hormone, PTH(1-34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et. al., *Bio. Med. Chem. Let.*, 9, 1003-1008 (1999) and Hamann, L. G. et. al., *J. Med. Chem.*, 42, 210-212 (1999).

A further use of the compounds of this invention is in combination with progesterone receptor agonists ("PRA"), such as levonorgestrel, medroxyprogesterone acetate (MPA).

The compounds of the present invention may be employed alone or in combination with each other and/or other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor agonists); anabolic agents; HIV or AIDS therapies; therapies useful in the treatment of Alzheimer's disease and other cognitive disorders; therapies useful in the treatment of sleeping disorders; anti-proliferative agents; and anti-tumor agents.

Examples of suitable anti-diabetic agents for use in combination with the compounds of the present invention include biguanides (e.g., metformin), glucosidase inhibitors (e.g., acarbose), insulins (including insulin secretagogues or insulin sensitizers), meglitinides (e.g., repaglinide), sulfonylureas (e.g., glimepiride, glyburide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 01/68603.

Examples of suitable anti-osteoporosis agents for use in combination with the compounds of the present invention include alendronate, risedronate, PTH, PTH fragment, raloxifene, calcitonins, steroidal or non-steroidal progesterone receptor agonists, RANK ligand antagonists, calcium sensing receptor antagonists, TRAP inhibitors, selective estrogen receptor modulators (SERM's), estrogen and AP-1 inhibitors.

Examples of suitable anti-obesity agents for use in combination with the compounds of the present invention include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993 (U. Cal SF), WO 99/00353 (KaroBio) and GB98/284425 (KaroBio), and/or an anorectic agent, such as dexamphetamine, phentermine, phenylpropanolamine or mazindol.

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Examples of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase (PDE) inhibitors for use in combination with the compounds of the present invention include PDE-3 inhibitors such as cilostazol, and phosphodiesterase-5 inhibitors (PDE-5 inhibitors) such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

Examples of suitable HIV or AIDS therapies for use in combination with the compounds of the present invention include indinavir sulfate, saquinavir, saquinavir mesylate, ritonavir, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, paclitaxel, FK-506, and adriamycin.

Examples of suitable anti-tumor agents for use in combination with the compounds of the present invention include paclitaxel, adriamycin, epothilones, cisplatin and carboplatin.

Compounds of the present invention may further be used in combination with nutritional supplements such as those described in U.S. Pat. No. 5,179,080, especially in combination with whey protein or casein, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatinine, B-hyroxy-B-methylbutyriate (Juven) and coenzyme Q-10.

In addition, compounds of the present invention may be used in combination with therapeutic agents used in the treatment of sexual dysfunction, including but not limited to PDE-5 inhibitors, such as sildenafil or IC-351.

Compounds of the present invention may further be used in combination with antiresorptive agents, hormone replacement therapies, vitamin D analogues, elemental calcium and calcium supplements, cathepsin K inhibitors, MMP inhibitors, vitronectin receptor antagonists, Src $SH_2$ antagonists, vacular—$H^+$-ATPase inhibitors, ipriflavone, fluoride, Tibo lone, pro stanoids, 17-beta hydroxysteroid dehydrogenase inhibitors and Src kinase inhibitors.

Compounds of the present invention may be used in combination with male contraceptives, such as nonoxynol 9 or therapeutic agents for the treatment of hair loss, such as minoxidil and finasteride or chemotherapeutic agents, such as with LHRH agonists.

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α-reductase inhibitors; inhibitors of 17β-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, 0lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. Patent can be employed together with any NHR modulators (including, but not limited to, those of present invention) such as AR modulators, ER modulators, with LHRH modulators, or with surgical castration, especially in the treatment of cancer).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for an adult human of from about 0.01 to 2000 mg of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

Transactivation Assays

AR Specific Assay

Compounds of the present invention were tested in transactivation assays of a transfected reporter construct and using the endogenous androgen receptor of the host cells. The transactivation assay provides a method for identifying functional agonists and partial agonists that mimic, or antagonists that inhibit, the effect of native hormones, in this case, dihydrotestosterone (DHT). This assay can be used to predict in vivo activity as there is a good correlation in both series of data. See, e.g. T. Berger et al., *J. Steroid Biochem. Molec. Biol.* 773 (1992), the disclosure of which is herein incorporated by reference.

For the transactivation assay a reporter plasmid is introduced by transfection (a procedure to induce cells to take foreign genes) into the respective cells. This reporter plasmid, comprising the cDNA for a reporter protein, such as secreted alkaline phosphatase (SEAP), controlled by prostate specific antigen (PSA) upstream sequences containing androgen response elements (AREs). This reporter plasmid functions as a reporter for the transcription-modulating activity of the AR. Thus, the reporter acts as a surrogate for the products (mRNA then protein) normally expressed by a gene under control of the AR and its native hormone. In order to detect antagonists, the transactivation assay is carried out in the presence of constant concentration of the natural AR hormone (DHT) known to induce a defined reporter signal. Increasing concentrations of a suspected antagonist will decrease the reporter signal (e.g., SEAP production). On the other hand, exposing the transfected cells to increasing concentrations of a suspected agonist will increase the production of the reporter signal.

For this assay, LNCaP and NDA 453 cells were obtained from the American Type Culture Collection (Rockville, Md.), and maintained in RPMI 1640 or DMEM medium supplemented with 10% fetal bovine serum (FBS; Gibco) respectively. The respective cells were transiently transfected by electroporation according to the optimized procedure described by Heiser, 130 Methods Mol. Biol., 117 (2000), with the pSEAP2/PSA540/Enhancer reporter plasmid. The reporter plasmid, was constructed as follows: commercial human placental genomic DNA was used to generate by Polymerase Cycle Reaction (PCR) a fragment containing the BglII site (position 5284) and the Hind III site at position 5831 of the human prostate specific antigen promoter (Accession # U37672), Schuur, et al., *J. Biol. Chem.*, 271 (12): 7043-51 (1996). This fragment was subcloned into the pSEAP2/basic (Clontech) previously digested with BglII and HindIII to generate the pSEAP2/PSA540 construct. Then a fragment bearing the fragment of human PSA upstream sequence between positions −5322 and −3873 was amplified by PCR from human placental genomic DNA. A XhoI and a BglII sites were introduced with the primers. The resulting fragment was subcloned into pSEAP2/PSA540 digested with XhoI and BglII respectively, to generate the pSEAP2/PSA540/Enhancer construct. LNCaP and MDA MB-453 cells were collected in media containing 10% charcoal stripped FBS. Each cell suspension was distributed into two Gene Pulser Cuvetts (Bio-Rad) which then received 8 μg of the reporter construct, and electoporated using a Bio-Rad Gene Pulser at 210 volts and 960 μFaraday. Following the transfections the cells were washed and incubated with media containing charcoal stripped fetal bovine serum in the absence (blank) or presence (control) of 1 nM dihydrotestosterone (DHT; Sigma Chemical) and in the presence or absence of the standard anti-androgen bicalutamide or compounds of the present invention in concentrations ranging from $10^{-10}$ to $10^{-5}$ M (sample). Duplicates were used for each sample. The compound dilutions were performed on a Biomek 2000 laboratory workstation.

After 48 h, a fraction of the supernatant was assayed for SEAP activity using the Phospha-Light Chemiluminescent Reporter Gene Assay System (Tropix, Inc). Viability of the remaining cells was determined using the CellTiter 96 Aqueous Non-Radioactive Cell Proliferation Assay (MTS Assay, Promega). Briefly, a mix of a tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS) are added to the cells. MTS (Owen's reagent) is bioreduced by cells into a formazan that is soluble in tissue culture medium, and therefore its absorbance at 490 nm can be measured directly from 96 well assay plates without additional processing. The quantity of formazan product as measured by the amount of 490 nm absorbance is directly proportional to the number of living cells in culture. For each replicate the SEAP reading was normalized by the Abs490 value derived from the MTS assay. For the antagonist mode, the % Inhibition was calculated as:

% Inhibition=100×(1−[average control−average blank/average sample−average blank])

Data was plotted and the concentration of compound that inhibited 50% of the normalized SEAP was quantified ($IC_{50}$).

For the agonist mode % Control was referred as the effect of the tested compound compared to the maximal effect observed with the natural hormone, in this case DHT, and was calculated as:

% Control=100×average sample−average blank/average control−average blank

Data was plotted and the concentration of compound that activates to levels 50% of the normalized SEAP for the control was quantified ($EC_{50}$).

GR Specificity Assay

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR see, e.g. G. Chalepakis et al., Cell, 53(3), 371 (1988). This plasmid was transfected into A549 cells, which expresses endogenous GR, to obtain a GR specific transactivation assay. A549 cells were obtained from the American Type Culture Collection (Rockville, Md.), and maintained in RPMI 1640 supplemented with 10% fetal bovine serum (FBS; Gibco). Determination of the GR specific antagonist activity of the compounds of the present invention was identical to that described for the AR specific transactivation assay, except that the DHT was replaced with 5 nM dexamethasone (Sigma Chemicals), a specific agonist for GR. Determination of the GR specific agonist activity of the compounds of the present invention was performed as described for the AR transactivation assay, wherein one measures the activation of the GR specific reporter system by the addition of a test compound, in the absence of a known GR specific agonists ligand.

PR Specific Assay

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HRE's) that can be regulated by both GR and PR. This plasmid was transfected into T47D, which expresses endogenous PR, to obtain a PR specific transactivation assay. T47D cells were obtained from the American Type Culture Collection (Rockville, Md.), and maintained in DMEM medium supplemented with 10% fetal bovine serum (FBS; Gibco). Determination of the PR specific antagonist activity of the compounds of the present invention was identical to that described for the AR specific transactivation assay, except that the DHT was replaced with 1 nM Promegastone (NEN), a specific agonist for PR. Determination of the PR specific agonist activity of the compounds of the present invention was performed as described for the AR transactivation assay, wherein one measures the activation of the PR specific reporter system by the addition of a test compound, in the absence of a known PR specific agonists ligand.

AR Binding Assay

For the whole-cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, were incubated at 37° C. to remove any endogenous ligand that might be complexed with the receptor in the cells. After 48 h, either a saturation analysis to determine the $K_d$ for tritiated dihydrotestosterone, [$^3$H]-DHT, or a competitive binding assay to evaluate the ability of test compounds to compete with [$^3$H]-DHT were performed. For the saturation analysis, media (RPMI 1640 or DMEM—0.2% CA-FBS) containing [$^3$H]-DHT (in concentrations ranging from 0.1 nM to 16 nM) in the absence (total binding) or presence (non-specific binding) of a 500-fold molar excess of unlabeled DHT were added to the cells. After 4 h at 37° C., an aliquot of the total binding media at each concentration of [$^3$H]-DHT was removed to estimate the amount of free [$^3$H]-DHT. The remaining media was removed, cells were washed three times with PBS and harvested onto UniFilter GF/B plates (Packard), Microscint (Packard) was added and plates counted in a Top-Counter (Packard) to evaluate the amount of bound [$^3$H]-DHT.

For the saturation analysis, the difference between the total binding and the non-specific binding, was defined as specific binding. The specific binding was evaluated by Scatchard analysis to determine the $K_d$ for [$^3$H]-DHT. See e.g. D. Rodbard, Mathematics and statistics of ligand assays: an illustrated guide: In: J. Langon and J. J. Clapp, eds., Ligand Assay, Masson Publishing U.S.A., Inc., New York, pp. 45-99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M were added to the cells. Two replicates were used for each sample. After 4 h at 37° C., cells were washed, harvested and counted as described above. The data was plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand was quantified ($IC_{50}$) after log-logit transformation. The $K_I$ values were determined by application of the Cheng-Prusoff equation to the $IC_{50}$ values, where:

$$K_I = \frac{IC_{50}}{(1 + (^3H-DHT)/K_d \text{ for } ^3H-DHT)}.$$

After correcting for non-specific binding, $IC_{50}$ values were determined. The $IC_{50}$ is defined as the concentration of competing ligand needed to reduce specific binding by 50%. The $K_d$s for [$^3$H]-DHT for MDA 453 and LNCaP were 0.7 and 0.2 nM respectively.

C2C12 Mouse Myoblast Transactivation Assay

Two functional transactivation assays were developed to assess the efficacy of androgen agonists in a muscle cell background using a luciferase reporter. The first assay (ARTA Stable 1) uses a cell line, Stable 1 (clone #72), which expresses the full length rat androgen receptor but requires the transient transfection of an enhancer/reporter. This cell line was derived from C2C12 mouse moyoblast cells. The second assay (ARTA Stable 2) uses a cell line, Stable 2 (clone #133), derived from Stable 1 which expresses both rAR and the enhancer/luciferase reporter.

The enhancer/reporter construct used in this system is pGL3/2XDR-1/luciferase. 2×DR-1 was reported to be an AR specific response element in CV-1 cells, Brown et. al. The Journal of Biological Chemistry 272, 8227-8235, (1997). It was developed by random mutagenesis of an AR/GR consensus enhancer sequence.

ARTA Stable 1

1. Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5× Antibiotic-Antimycotic, and 800 µg/mL Geneticin (Gibco BRL, Cat. No.: 10131-035).

2. 48 h later, cells are transfected with pGL3/2XDR-1/luciferase using LipofectAMINE Plus™ Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 µl/well Opti-MEMem media (Gibco BRL, Cat. No.: 31985-070). To this, 0.5 µl/well Plus reagent is added. This mixture is incubated for 15 min at rt. In a separate vessel, 0.385 µl/well LipofectAMINE reagent is diluted with 5 µl/well Opti-MEM. The DNA mixture is then combined with the LipofectAMINE mixture and incubated for an additional 15 min at rt. During this time, the media from the cells is removed and replaced with 60 µl/well of Opti-MEM. To this is added 10 µl/well of the DNA/LipofectAMINE transfection mixture. The cells are incubated for 4 h.

3. The transfection mixture is removed from the cells and replaced with 90 µl of media as in #1 above.

4. 10 µl/well of appropriate drug dilution is placed in each well.

5. 24 h later, the Steady-Glo™ Luciferase Assay System is used to detect activity according to the manufacturer's instructions (Promega, Cat. No.: E2520).

ARTA Stable 2

1. Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×

MEM Na Pyruvate (Gibco BRL, Cat. No.: 11360-070), 0.5× Antibiotic-Antimycotic, 800 µg/mL Geneticin (Gibco BRL, Cat. No.: 10131-035) and 800 µg/mL Hygromycin β (Gibco BRL, Cat. No.: 10687-010).

2. 48 h later, the media on the cells is removed and replaced with 90 µl fresh. 10 µl/well of appropriate drug dilution is placed in each well.

3. 24 h later, the Steady-Glo™ Luciferase Assay System is used to detect activity according to the manufacturer's instructions (Promega, Cat. No. E2520).

Proliferation Assays

Human Prostate Cell Proliferation Assay

Compounds of the present invention were tested ("test compounds") on the proliferation of human prostate cancer cell lines. For that, MDA PCa2b cells, a cell line derived from the metastasis of a patient that failed castration, Navone et al., Clin. Cancer Res., 3, 2493-500 (1997), were incubated with or without the test compounds for 72 h and the amount of [$^3$H]-thymidine incorporated into DNA was quantified as a way to assess number of cells and therefore proliferation. The MDA PCa2b cell line was maintained in BRFF-HPC1 media (Biological Research Faculty & Facility Inc., MD) supplemented with 10% FBS. For the assay, cells were plated in Biocoated 96-well microplates and incubated at 37° C. in 10% FBS (charcoal-stripped)/BRFF-BMZERO (without androgens). After 24 h, the cells were treated in the absence (blank) or presence of 1 nM DHT (control) or with test compounds (sample) of the present invention in concentrations ranging from $10^{-10}$ to $10^{-5}$ M. Duplicates were used for each sample. The compound dilutions were performed on a Biomek 2000 laboratory work station. Seventy-two h later 0.44 uCi of [$^3$H]-Thymidine (Amersham) was added per well and incubated for another 24 h followed by tripsinization, harvesting of the cells onto GF/B filters. Micro-scint PS were added to the filters before counting them on a Beckman Top-Count.

The % Inhibition was calculated as:

% Inhibition=100×(1−[average$_{control}$−average$_{blank}$/average$_{sample}$−average$_{blank}$])

Data was plotted and the concentration of compound that inhibited 50% of the [$^3$H]-Thymidine incorporation was quantified (IC$_{50}$).

Murine Breast Cell Proliferation Assay

The ability of compounds of the present invention ("test compounds") to modulate the function of the AR was determined by testing said compounds in a proliferation assay using the androgen responsive murine breast cell line derived from the Shionogi tumor, Hiraoka et al., Cancer Res., 47, 6560-6564 (1987). Stable AR dependent clones of the parental Shionogi line were established by passing tumor fragments under the general procedures originally described in Tetuo, et. al., Cancer Research 25, 1168-1175 (1965). From the above procedure, one stable line, SC114, was isolated, characterized and utilized for the testing of example compounds. SC114 cells were incubated with or without the test compounds for 72 h and the amount of [3H]-thymidine incorporated into DNA was quantified as a surrogate endpoint to assess the number of cells and therefore the proliferation rate as described in Suzuki et. al., J. Steroid Biochem. Mol. Biol. 37, 559-567 (1990). The SC114 cell line was maintained in MEM containing $10^{-8}$ M testosterone and 2% DCC-treated FCS. For the assay, cells were plated in 96-well microplates in the maintenance media and incubated at 37° C. On the following day, the medium was changed to serum free medium [Ham's F-12:MEM (1;1, v/v) containing 0.1% BSA] with (antagonist mode) or without (agonist mode) $10^{-8}$ M testosterone and the test compounds of the present invention in concentrations ranging from $10^{10}$ to $10^{-5}$ M. Duplicates were used for each sample. The compound dilutions were performed on a Biomek 2000 laboratory work station. Seventy two h later 0.44 uCi of [3H]-Thymidine (Amersham) was added per well and incubated for another 2 h followed by tripsinization, and harvesting of the cells onto GF/B filters. Micro-scint PS were added to the filters before counting them on a Beckman TopCount.

For the antagonist mode, the % Inhibition was calculated as:

% Inhibition=100×(1−[average$_{sample}$−average$_{blank}$/average$_{control}$−average$_{blank}$])

Data was plotted and the concentration of compound that inhibited 50% of the [$^3$H]-Thymidine incorporation was quantified (IC$_{50}$).

For the agonist mode % Control was referred as the effect of the tested compound compared to the maximal effect observed with the natural hormone, in this case DHT, and was calculated as:

% Control=100×(average$_{sample}$−average$_{blank}$)/(average$_{control}$−average$_{blank}$)

Data was plotted and the concentration of compound that inhibited 50% of the [$^3$H]-Thymidine incorporation was quantified (EC$_{50}$).

In Vitro Assay to Measure GR-Induced AP-1 Transrepression

The AP-1 assay is a cell-based luciferase reporter assay. A549 cells, which contain endogenous glucocorticoid receptor, were stably transfected with an AP-1 DNA binding site attached to the luciferase gene. Cells are then grown in RPMI+10% fetal calf serum (charcoal-treated)+Penicillin/Streptomycin with 0.5 mg/mL geneticin. Cells are plated the day before the assay at approximately 40000 cells/well. On assay day, the media is removed by aspiration and 20 µL assay buffer (RPMI without phenol red+10% FCS (charcoal-treated)+Pen/Strep) is added to each well. At this point either 20 µL assay buffer (control experiments), the compounds of the present invention ("test compounds") (dissolved in DMSO and added at varying concentrations) or dexamethasome (100 nM in DMSO, positive control) are added to each well. The plates are then pre-incubated for 15 min at 37° C., followed by stimulation of the cells with 10 ng/mL PMA. The plates are then incubated for 7 h at 37° C. after which 40 µL luciferase substrate reagent is added to each well. Activity is measured by analysis in a luminometer as compared to control experiments treated with buffer or dexamethasone. Activity is designated as % inhibition of the reporter system as compared to the buffer control with 10 ng/mL PMA alone. The control, dexamethasone, at a concentration of ≦10 µM typically suppresses activity by 65%. Test compounds which demonstrate an inhibition of PMA induction of 50% or greater at a concentration of test compound of ≦10 µM are deemed active.

In Vivo Assays

Levator Ani & Wet Prostate Weight Assay AR Agonist Assay

The activity of compounds of the present invention as AR agonists was investigated in an immature male rat model, a recognized test of anabolic effects in muscle and sustaining effects in sex organs for a given compound, as described in L. G. Hershberger et al., Proc. Soc. Expt. Biol. Med., 83, 175 (1953); B. L. Beyler et al, "Methods for evaluating anabolic and catabolic agents in laboratory animals", J. Amer. Med. Women's Ass., 23, 708 (1968); H. Fukuda et al., "Investigations of the levator ani muscle as an anabolic steroid assay", *Nago Dai. Yak. Ken. Nem.* 14, 84 (1966) the disclosures of which are herein incorporated by reference.

The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T results in a reversal of muscular atrophy. The effects of T on muscular atrophy in the rat levator ani muscle have been well characterized. M. Masuoka et al., "Constant cell population in normal, testosterone deprived and testosterone stimulated levator ani muscles" *Am. J. Anat.* 119, 263 (1966); Z. Gori et al., "Testosterone hypertrophy of levator ani muscle of castrated rats. I. Quantitative data" *Boll.-Soc. Ital. Biol. Sper.* 42, 1596 (1966); Z. Gori et al., "Testosterone hypertrophy of levator ani muscle of castrated rats. II. Electron-microscopic observations" *Boll.-Soc. Ital. Biol. Sper.* 42, 1600 (1966); A. Boris et al., *Steroids* 15, 61 (1970). As described above, the effects of androgens on maintenance of male sexual accessory organs, such as the prostate and seminal vesicles, is well described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats. Sexually mature rats (200-250 g, 6-8 weeks-old, Sprague-Dawley, Harlan) were acquired castrated from the vendor (Taconic). The rats were divided into groups and treated daily for 7 to 14 days with one of the following:

1. Control vehicle
2. Testosterone Propionate (TP) (3 mg/rat/day, subcutaneous)
3. TP plus Bicalutamide (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 7-14-day treatment, the animals were sacrificed by carbon dioxide, and the levator ani, seminal vesicle and ventral prostate weighed. To compare data from different experiments, the levator ani muscle and sexual organ weights were first standardized as mg per 100 g of body weight, and the increase in organ weight induced by TP was considered as the maximum increase (100%). Super-anova (one factor) was used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases levator ani, seminal vesicles (SV) and prostate in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 h after subcutaneous injection than that of TP, thereafter, these high levels declined very rapidly. In contrast, the serum concentrations of T and DHT in TP-treated animals were fairly consistent during the 24 h, and therefore, TP showed about 10-30-fold higher potency than free T.

EXAMPLES

The following examples serve to better illustrate, but not limit, some of the preferred embodiments of the invention.

Examples 1 and 2

2-Chloro-4-((3aR,4R,6aS)-4-hydroxy-1-oxo-hexahydrocyclopenta[c]pyrrol-2(1H)-yl)-3-methylbenzonitrile and 2-Chloro-4-((3aS,4S,6aR)-4-hydroxy-1-oxo-hexahydrocyclopenta[c] pyrrol-2(1H)-yl)-3-methylbenzonitrile

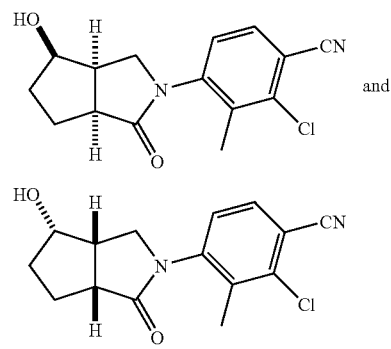

Examples 3 and 4

2-Chloro-4-((3aS,4R,6aS)-4-hydroxy-2-oxo-hexahydrocyclopenta[b]pyrrol-1(2H)-yl)-3-methylbenzonitrile and 2-Chloro-4-((3aR,4S,6aR)-4-hydroxy-2-oxo-hexahydrocyclopenta[b]pyrrol-1(2H)-yl)-3-methylbenzonitrile

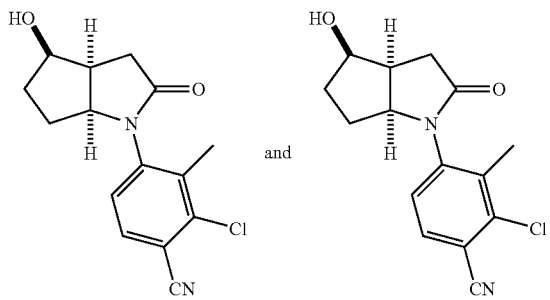

1A. 3-Chloro-2-methylphenylacetamide

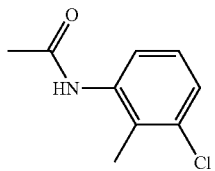

To a solution of 3-chloro-2-methylaniline (3.0 g, 21.2 mmol) in 25 mL of EtOH at rt was added acetic anhydride (2.4 mL, 25.4 mmol), and the solution was stirred at rt for 2 h. The mixture was concentrated under reduced pressure to give 3.89 g (100%) of the desired acetamide. $^1$H NMR (DMSO-$d_6$) δ 2.05 (s, 3H), 2.20 (s, 3H), 7.16 (t, J=7.7, 8.3, 1H), 7.25 (d, J=8.3, 1H), 7.31 (d, J=8.3, 1H), 9.55 (s, 1H); $^{13}$C NMR (DMSO-$d_6$) δ 15.1, 23.1, 124.4, 125.8, 126.7, 130.3, 133.7, 138.0, 168.3; HPLC a) column: Phenominex ODS C18 4.6×50 mm, 4 min gradient, 10% MeOH/90% H$_2$O/0.1% TFA to 90% MeOH/10% H$_2$O/0.1% TFA; 1 min hold, 4 mL/min UV detection at 220 nm, 2.32 min retention time; HPLC b) column: Shimadzu Shim-Pack VP-ODS C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 2.20 min retention time (99%); MS (ES) m/z 184 [M+H]$^+$.

1B. 4-Bromo-3-chloro-2-methylphenylacetamide

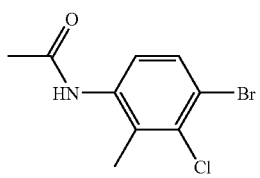

To a suspension of acetamide 1A (2.0 g, 10.9 mmol) in 15 mL of glacial AcOH cooled to approximately 15° C. was added bromine (1.67 mL, 32.7 mmol) over 20 min. The ice bath was removed and the solution was stirred for 2 h, poured into ice water with stirring, and the solid was then filtered and dried to give 2.75 g (96%) of the desired bromide. $^1$H NMR (DMSO-$d_6$) δ 2.05 (s, 3H), 2.28 (s, 3H), 7.29 (d, J=8.3, 1H), 7.56 (d, J=8.8, 1H), 9.60 (s, 1H); $^{13}$C NMR (DMSO-$d_6$) δ 16.7, 23.1, 118.1, 125.5, 130.4, 132.7, 133.4, 137.1, 168.4; HPLC a) column: Phenominex ODS C18 4.6×50 mm, 4 min gradient, 10% MeOH/90% H$_2$O/0.1% TFA to 90% MeOH/10% H$_2$O/0.1% TFA, 1 min hold, 4 mL/min, UV detection at 220 nm, 2.95 min retention time; HPLC b) column: Shimadzu Shim-Pack VP-ODS C18 4.6×50 mm, 4 min gradient, 10% MeOH/90% H$_2$O/0.1% TFA to 90% MeOH/10% H$_2$O/0.1% TFA, 1 min hold, 4 mL/min, UV detection at 220 nm, 2.87 min retention time (98%); MS (ES) m/z 263 [M+H]$^+$.

1C. 3-Chloro-4-cyano-2-methylphenylacetamide

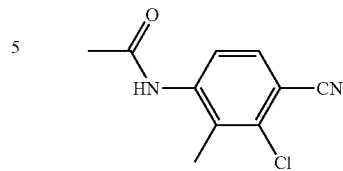

A suspension of bromide 1B (2.7 g, 10.3 mmol) and copper cyanide (0.92 g, 10.3 mmol) in DMF (30 mL) was heated to 150° C. for 4 h. The suspension was cooled, poured into water with stirring, and the solid was filtered and dried to give 1.44 g (67%) of the desired nitrile. $^1$H NMR (DMSO-$d_6$) δ 2.12 (s, 3H), 2.29 (s, 3H), 7.72 (d, J=8.8, 11H), 7.75 (d, J=8.2, 11H), 9.73 (s, 1H); $^{13}$C NMR (DMSO-$d_6$) δ 15.3, 23.5, 107.7, 116.5, 123.0, 130.1, 131.5, 135.7, 142.3, 168.8; HPLC a) column: Phenominex ODS C18 4.6×50 mm, 4 min gradient, 10% MeOH/90% H$_2$O/0.1% TFA to 90% MeOH/10% H$_2$O/0.1% TFA, 1 min hold, 4 mL/min, UV detection at 220 nm, 2.23 min retention time; HPLC b) column: Shimadzu Shim-Pack VP-ODS C18 4.6×50 mm, 4 min gradient, 10% MeOH/90% H$_2$O/0.1% TFA to 90% MeOH/10% H$_2$O/0.1% TFA, 1 min hold, 4 mL/min, UV detection at 220 nm, 2.13 min retention time (95%); MS (ES) m/z 209 [M+H]$^+$.

1D. 3-Chloro-4-cyano-2-methylphenylaniline

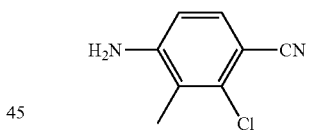

A solution of cyanoacetamide 1C (9.90 g, 47.4 mmol) in 100 mL of concentrated HCl/EtOH (1:1) was refluxed 30 min. The solution was then concentrated and dried under reduced pressure to give 9.41 g (98%) of the desired aniline as the hydrochloride salt. The free base of the aniline was obtained by suspending the salt in EtOAc and washing with saturated aqueous NaHCO$_3$ solution. The organic layer was then dried (MgSO$_4$), filtered and concentrated under reduced pressure. $^1$H NMR (DMSO-$d_6$) δ 2.12 (s, 3H), 6.30 (s, 2H), 6.61 (d, J=8.23, 1H), 7.36 (d, J=8.23, 1H); $^{13}$C NMR (DMSO-$d_6$) δ 13.8, 96.9, 112.1, 118.3, 118.85, 132.2, 135.6, 152.5; HPLC a) column: Phenominex ODS C18 4.6×50 mm, 4 min gradient, 10% MeOH/90% H$_2$O/0.1% TFA to 90% MeOH/10% H$_2$O/0.1% TFA, 1 min hold, 4 mL/min, UV detection at 220 nm, 2.43 min retention time; HPLC b):column: Shimadzu Shim-Pack VP-ODS C18 4.6×50 mm, 4 min gradient, 10% MeOH/90% H$_2$O/0.1% TFA to 90% MeOH/10% H$_2$O/0.1% TFA, 1 min hold, 4 mL/min, UV detection at 220 nm, 2.31 min retention time (99%); MS (ES) m/z 167 [M+H]$^+$.

1E. 2-Chloro-4-Iodo-3-methylbenzonitrile

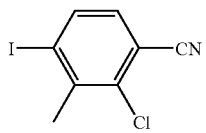

To a suspension of CuI (7.5 g, 39.3 mmol) in acetonitrile (150 mL) under N$_2$ at rt was added tert-butylnitrite (5.7 mL, 47.9 mmol). The reaction mixture was heated to 65° C. for 1 h and then compound 1D (6.0 g, 36.0 mmol) was added and the reaction was heated at 65° C. for 3 h. The reaction was cooled to rt and filtered through a pad of celite. The celite pad was washed with EtOAc. The organics were washed twice with water, dried over MgSO$_4$, filtered and concentrated. Purification by flash chromatography (silica gel, 110 g ISCO, 0-5% EtOAc in hexane, step gradient) gave the title compound (4.3 g): MS (ES) m/z 278 [M+H]$^+$.

1F. 6,6-Diethoxybicyclo[3.2.0]heptan-2-one

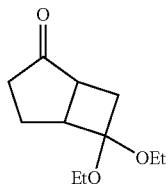

To a solution of cyclopent-2-enone (3.7 g, 45 mmol) in pentane (80 mL) was added 1,1-diethoxyethene (89 mL, 677 mmol). The mixture was put in an ACE Photo Reactor (450 W lamp), and stirred at RT for 20 hr. It was concentrated to give the title compound as a pale yellow oil.

1G. 2-Hydroxybicyclo[3.2.0]heptan-6-one

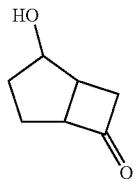

To a stirred solution of compound 1F in dioxane (50 mL) and 2M KH$_2$PO$_4$ (50 mL) was added NaBH$_4$ (1.0 g, 26.4 mmol) over a 10 min-period, and the stirring was continued at RT for 1 hr. The reaction mixture was diluted with 2M HCl to adjust pH to 1, and stirred at RT for another 1 hr. The reaction was concentrated, dissolved in EtOAc, washed with water, dried over Na$_2$SO$_4$, and concentrated. Purification by silica gel chromatography (50% EtOAc in hexanes) provided the title compound (1.9 g) as a pale yellow oil.

1H. 6-Oxobicyclo[3.2.0]heptan-2-yl benzoate

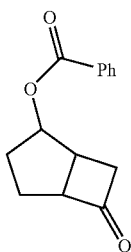

To a stirred solution of compound 1G (1.9 g, 15.1 mmol) in CH$_2$Cl$_2$ (10 mL) at 0° C. under nitrogen were added Et$_3$N (3.1 mL, 22.2 mmol) and benzoyl chloride (2.33 g, 16.6 mmol). The reaction was stirred at 0° C. for 60 min and RT for 30 min, then quenched with water. The product was extracted with CH$_2$Cl$_2$, the organics were washed with saturated aqueous NaHCO$_3$, dried over Na$_2$SO$_4$, and concentrated. Purification by silica gel chromatography (5% EtOAc in hexanes) provide the title compound (3 g).

1I. 1-Oxo-octahydrocyclopenta[c]pyrrol-4-yl benzoate and

1J. 2-Oxo-octahydrocyclopenta[b]pyrrol-4-yl benzoate

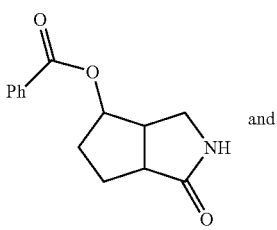
(1I)

and

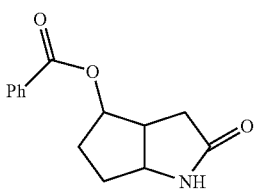
(1J)

To a stirred solution of compound 1H (500 mg, 2.2 mmol) in CH$_2$Cl$_2$ (5 mL) was added a solution of O-mesitylenesulfonylhydroxylamine (650 mg, 3 mmol) in CH$_2$Cl$_2$ (2 mL) at −10° C., and the stirring was continued for 20 min between −10 to 0° C. It was concentrated, added to a mixed solvent of benzene and methanol (30 mL, 3:1) followed by a slurry of basic alumina (25 g) in methanol (20 mL). The reaction mixture was stirred at RT overnight, and alumina solid was removed by filtration. Purification by silica gel chromatography (5% to 100% EtOAc in hexanes, then 5% methanol in EtOAc) provide mixtures of the title compounds 1I and 1J (total 360 mg) as a yellow oil. MS (ES) m/z 246 [M+H]$^+$.

1K. 2-(3-Chloro-4-cyano-2-methylphenyl)-1-oxo-octahydrocyclopenta[c]-pyrrol-4-yl benzoate and 1L. 1-(3-Chloro-4-cyano-2-methylphenyl)-2-oxo-octahydrocyclopenta[b]-pyrrol-4-yl benzoate

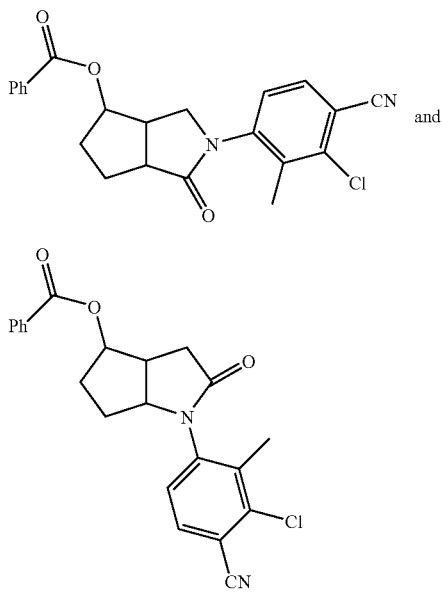

(1K)

(1L)

To a vial containing mixtures of compound 1I and 1J (100 mg, 0.4 mmol) obtained from previous step in dioxane (1 mL) were added CuI (15.6 mg, 0.08 mmol), K$_3$PO$_4$ (174 mg, 0.82 mmol), 1,2-cyclohexyldiamine (4.7 mg, 0.08 mmol) and compound 1E (136 mg, 0.49 mmol). The vial was sealed, and heated at 110° C. for 14 hr, cooled to RT. The solid was filtered off, and filtrate was concentrated. Purification by silica gel chromatography (5% to 100% EtOAc in hexanes, then 10% methanol in EtOAc) provide the mixtures of title compounds 1K and 1L (total 98 mg) as a yellow oil. MS (ES) m/z 395 [M+H]$^+$.

Chiral Separation of Compound 1K and 1L

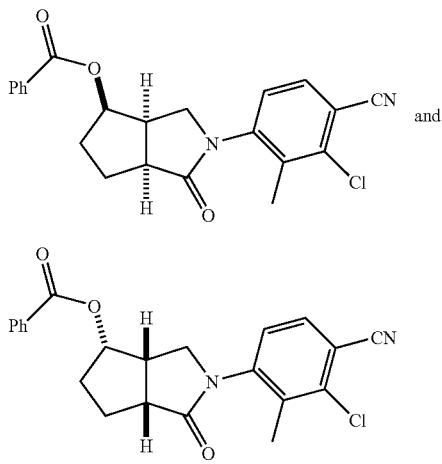

(1K-1)

(1K-2)

The enantiomer 1K-1 and 1K-2 were separated from the mixtures of compound 1K and 1L obtained in previous step.

The chiral separation was done on a Chiralpak AD column (20% IPA in heptane) and followed by Chiralpak OD (6% MeOH and 6% EtOH in heptane) to give 24 mg each.

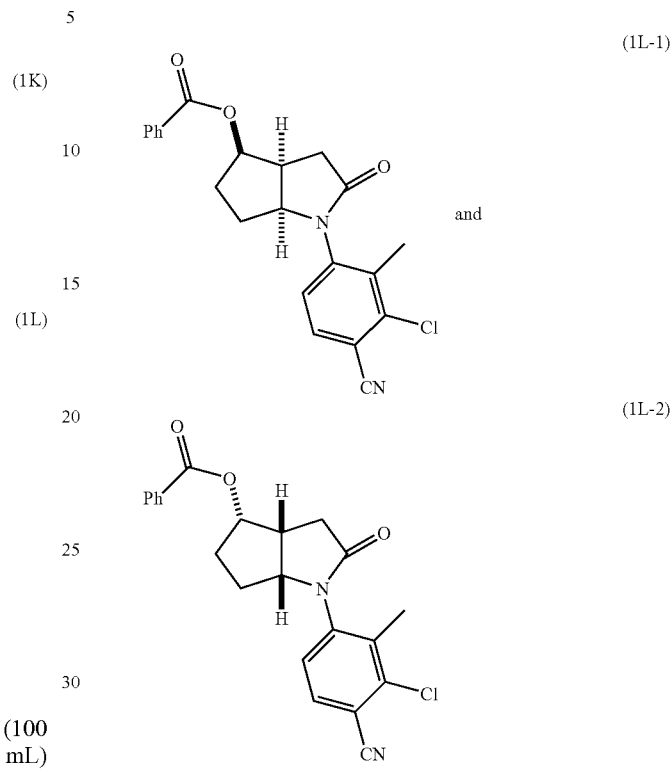

(1L-1)

(1L-2)

The enantiomer 1L-1 and 1L-2 were separated from the mixtures of compound 1K and 1L obtained in previous step. The chiral separation was done on a Chiralpak AD column (20% IPA in heptane) and followed by Chiralpak OD (6% MeOH and 6% EtOH in heptane) to give 10 mg each.

2-Chloro-4-((3aR,4R,6aS)-4-hydroxy-1-oxo-hexahydrocyclopenta[c]pyrrol-2(1H)-yl)-3-methylbenzonitrile (Example 1)

To a stirred solution of compound 1K-1 (24 mg, 0.06 mmol) in 2 mL of THF was added KOH (90 µL, 1M in methanol) at 0° C., and the stirring was continued at 0° C. for 3 hr. It was quenched with 1N HCl (90 µL), and diluted with EtOAc and water. The organic layer was separated, dried over Na$_2$SO$_4$, and concentrated. Purification by silica gel chromatography (100% CH$_2$Cl$_2$ to 5% MeOH in CH$_2$Cl$_2$ or 5%-80% EtOAc in hexanes) provide the title compound. MS (ES) m/z 291 [M+H]$^+$; [α]=−80° (589 nm, c=0.091 in MeOH);

2-Chloro-4-((3aS,4S,6aR)-4-hydroxy-1-oxo-hexahydrocyclopenta[c]pyrrol-2(1H)-yl)-3-methylbenzonitrile (Example 2)

The title compound was prepared from compound 1K-2 in a similar manner as for example 1 (last step). MS (ES) m/z 291 [M+H]$^+$; [α]=+80° (589 nm, c=0.091 in MeOH).

2-Chloro-4-((3aS,4R,6aS)-4-hydroxy-2-oxo-hexahydrocyclopenta[b]pyrrol-1(2H)-yl)-3-methylbenzonitrile (Example 3)

The title compound was prepared from compound 1L-1 in a similar manner as for example 1 (last step). MS (ES) m/z 291 [M+H]$^+$; [α]=+13.2° (589 nm, c=0.092 in MeOH).

2-Chloro-4-((3aR,4S,6aR)-4-hydroxy-2-oxo-hexahydrocyclopenta[b]-pyrrol-1(2H)-yl)-3-methylbenzonitrile (Example 4)

The title compound was prepared from compound 1L-2 in a similar manner as for example 1 (last step). MS (ES) m/z 291 [M+H]⁺; [α]=−13.5 (589 nm, c=0.092 in MeOH).

Example 5

2-Chloro-4-((3aR,4S,6aS)-4-hydroxy-1-oxo-hexahydrocyclopenta[c]pyrrol-2(1H)-yl)-3-methylbenzonitrile

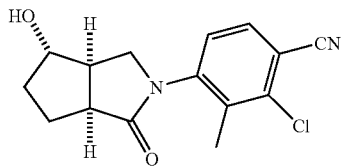

5A. (3aR,4S,6aS)-2-(3-Chloro-4-cyano-2-methylphenyl)-1-oxo-octahydrocyclopenta[c]pyrrol-4-ylbenzoate

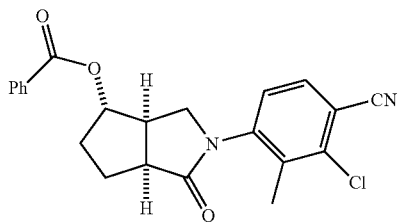

To a solution of example 1 (10 mg, 0.034 mmol) in 1 mL of THF were added triphenylphosphine (18 mg, 0.069 mmol), benzoic acid (8.4 mg, 0.069 mmol) and diisopropyl azodicarboxylate (13.9 mg, 0.069 mmol), and stirred at RT for 3 hr. It was concentracted, and purified by prepHPLC to give the title compound (11 mg). MS (ES) m/z 395 [M+H]⁺.

5B. 2-Chloro-4-((3aR,4S,6aS)-4-hydroxy-1-oxo-hexahydrocyclopenta[c]pyrrol-2(1H)-yl)-3-methylbenzonitrile (example 5)

The title compound was prepared from compound 5A in a similar manner as for Example 1 (last step). MS (ES) m/z 291 [M+H].

Example 6

2-Chloro-4-((3aS,4R,6aR)-4-hydroxy-1-oxo-hexahydrocyclopenta[c]pyrrol-2(1H)-yl)-3-methylbenzonitrile

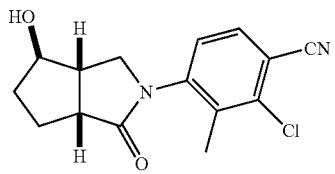

The title compound was prepared from the final compound obtained from example 2 in a similar manner as for example 5. MS (ES) m/z 291 [M+H].

Examples 7 and 8

2-Chloro-4-(((3aR,4R,6aS)-4-hydroxy-1-oxo-hexahydrocyclopenta-[c]pyrrol-2(1H)-yl)methyl)-3-methylbenzonitrile and 2-Chloro-4-(((3aS,4S,6aR)-4-hydroxy-1-oxo-hexahydrocyclopenta [c]pyrrol-2(1H)-yl)methyl)-3-methylbenzonitrile

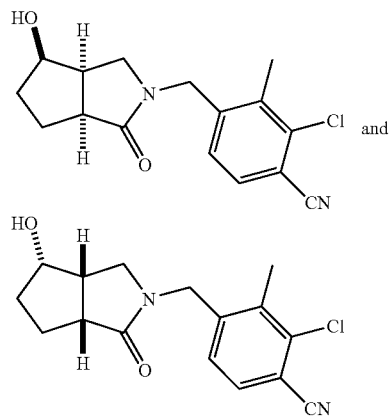

Examples 9 and 10

6-Chloro-3-(((3aS,4R,6aS)-4-hydroxy-2-oxo-hexahydrocyclopenta[b]-pyrrol-1(2H)-yl)methyl)-2-methylbenzonitrile and 6-Chloro-3-(((3aR,4S,6aR)-4-hydroxy-2-oxo-hexahydrocyclopenta[b]pyrrol-1(2H)-yl)methyl)-2-methylbenzonitrile

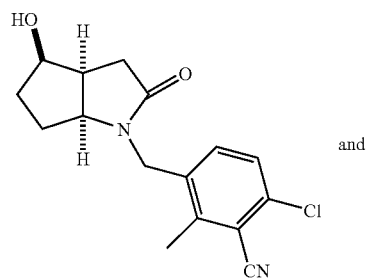

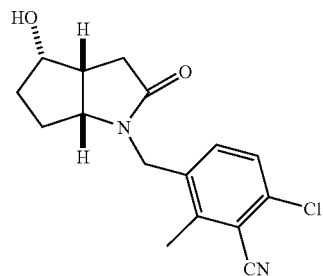

7A. Methyl 3-chloro-4-cyano-2-methylbenzoate

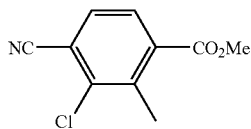

To a solution of compound 1E (5 g, 14.4 mmol) in DMF (80 mL) and MeOH (60 mL) were added 1,3-bis(diphenylphosphino)propane (1.78 g, 4.3 mmol), palladium acetate (968 mg, 4.3 mmol) and DBU (3.28 g, 21.6 mmol). The flask was flushed with carbon monoxide (CO) several times, then heated at 80° C. overnight under a CO balloon. The catalyst was filtered, and the filtrate was concentrated. The residue was dissolved in EtOAc, washed with water, dried over $Na_2SO_4$, and concentrated. Purification by silica gel chromatography (0-10% EtOAc in hexanes) provide the title compound (2.75 g) as a light pink powder.

7B. 2-Chloro-4-(hydroxymethyl)-3-methylbenzonitrile

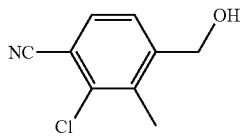

To a pressure reaction flask containing compound 7A (1.5 g, 7.2 mmol) in THF (30 mL) were added 1,2-ethanedithiol (2.4 g, 28.6 mmol) and $NaBH_4$ (812 mg, 21.5 mmol). It was sealed, and heated at 70° C. for 2 hr, and cooled to RT. The reaction mixture was concentrated, dissolved in EtOAc, washed with water, dried over $Na_2SO_4$, and concentrated. Recrystallization in EtOAc/hexanes give the title compound (870 mg). (ES) m/z 182 $[M+H]^+$; 204 $[M+Na]^+$.

7C. 4-(Bromomethyl)-2-chloro-3-methylbenzonitrile

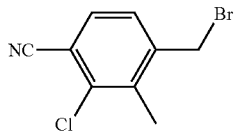

To a solution of compound 7B (700 mg, 3.9 mmol) in $CH_2Cl_2$ (15 mL) was added $PBr_3$ (5.8 mL, 5.8 mmol, 1N in $CH_2Cl_2$) at −15° C., and stirred at −15° C. for 3 hr. The reaction was slowly quenched with saturated $NaHCO_3$ solution at −15° C.

The organic layer was separated, dried over $MgSO_4$, and concentrated. Purification by silica gel chromatography (0-10% EtOAc in hexanes) provide the title compound (270 mg) as a white powder.

7D. 2-(3-Chloro-4-cyano-2-methylbenzyl)-1-oxo-octahydrocyclopenta[c]-20 pyrrol-4-yl benzoate and 7E. 1-(3-Chloro-4-cyano-2-methylbenzyl)-2-oxo-octahydrocyclopenta[b]-pyrrol-4-yl benzoate

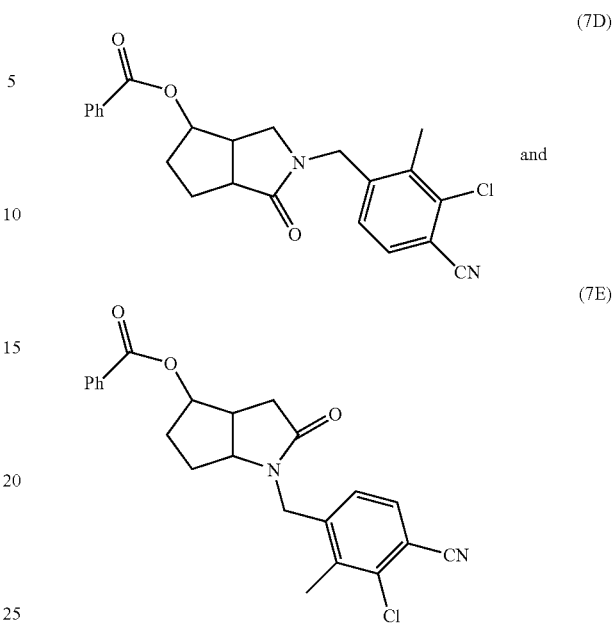

To a solution containing mixtures of compound 1I and 1J (170 mg, 0.69 mmol, different batch than previous lot in example 1) in anhydrous THF (4 mL) and anhydrous DMF (4 mL) was added sodium hydride (27.7 mg, 0.69 mmol) at 0° C., and stirred at 0° C. for 45 min. Compound 7C (169 mg, 0.69 mmol) was added at 0° C., the ice-water bath was removed, and the stirring was continued between 0° C. to RT for 2 hr before it was quenched with saturated $NH_4Cl$ solution. The mixture was diluted with EtOAc, organic layer was separated, washed with water, dried over $MgSO_4$, and concentrated. Purification by silica gel chromatography (30-100% EtOAc in hexanes) provide the title compound 7D (90 mg) and 7E (151 mg). Compound 7D: (ES) m/z 409 $[M+H]^+$. Compound 7E: (ES) m/z 409 $[M+H]^+$.

Chiral Separation of Compounds 7D and 7E

Both separations were done on a Chiralpak OD prep column (7.5% MeOH, 7.5% EtOH in heptane) to give 45 mg each of 7D1 and 7D2; 75 mg each of 7E1 and 7E2.

2-Chloro-4-(((3aR,4R,6aS)-4-hydroxy-1-oxo-hexahydrocyclopenta[c]-pyrrol-2(1H)-yl)methyl)-3-methylbenzonitrile (Example 7)

The title compound was prepared from compound 7D1 in a similar manner as for example 1 (last step). MS (ES) m/z 305 [M+H]; $[\alpha]$=−19.0° (589 nm, c=0.080 in $CH_2Cl_2$).

2-Chloro-4-(((3aS,4S,6aR)-4-hydroxy-1-oxo-hexahydrocyclopenta[c]-pyrrol-2(1H)-yl)methyl)-3-methylbenzonitrile The title compound was prepared from compound 7D2 in a similar manner as for example 1 (last step). MS (ES) m/z 305 [M+H]; $[\alpha]$=+21.3° (589 nm, c=0.081 in $CH_2Cl_2$).

6-Chloro-3-(((3aS,4R,6aS)-4-hydroxy-2-oxo-hexahydrocyclopenta[b]-pyrrol-1(2H)-yl)methyl)-2-methylbenzonitrile (Example 9)

The title compound was prepared from compound 7E1 in a similar manner as for example 1 (last step). MS (ES) m/z 305 [M+H]; $[\alpha]$=−24.5° (589 nm, c=0.087 in $CH_2Cl_2$).

6-Chloro-3-(((3aR,4S,6aR)-4-hydroxy-2-oxo-hexahydrocyclopenta[b]-pyrrol-1(2H)-yl)methyl)-2-methylbenzonitrile (Example 10)

The title compound was prepared from compound 7D2 in a similar manner as for example 1 (last step). MS (ES) m/z 305 [M+H]; [α]=+24.2° (589 nm, c=0.086 in $CH_2Cl_2$).

What is claimed is:

1. A compound according to formula I:

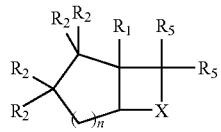

I or a pharmaceutically acceptable salt thereof, wherein $R_1$ is independently selected from the group consisting of H, alkyl, substituted alkyl, alkenyl, substituted alkenyl, arylalkyl, substituted arylalkyl, $CO_2R_4$, $CONR_4R_4'$, and $CH_2OR_4$;

$R_2$ is independently selected from the group consisting of alkyl, substituted alkyl, $OR_3$, $SR_3$, halo, $NHR_3$, $NHCOR_4$, $NHCO_2R_4$, $NHCONR_4R_4'$ and $NHSO_2R_4$;

$R_2'$ is independently selected from the group consisting of H, alkyl, substituted alkyl, $OR_3$, $SR_3$, halo, $NHR_3$, $NHCOR_4$, $NHCO_2R_4$, $NHCONR_4R_4'$ and $NHSO_2R_4$;

$R_2''$ is independently selected from the group consisting of H, alkyl, substituted alkyl, $OR_3$, $SR_3$, halo, $NHR_3$, $NHCOR_4$, $NHCO_2R_4$, $NHCONR_4R_4'$ and $NHSO_2R_4$;

$R_2'''$ is independently selected from the group consisting of H, alkyl, substituted alkyl, $OR_3$, $SR_3$, halo, $NHR_3$, $NHCOR_4$, $NHCO_2R_4$, $NHCONR_4R_4'$ and $NHSO_2R_4$;

$R_3$ is independently selected from the group consisting of H, alkyl, substituted alkyl, $CHF_2$, $CF_3$ and $COR_4$;

$R_4$ is independently selected from the group consisting of H, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;

$R_4'$ is independently selected from the group consisting of H, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;

$R_5$ is independently selected from the group consisting of H, $CF_3$, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;

$R_5'$ is independently selected from the group consisting of H, $CF_3$, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;

X is —C(=O)—N($R_6$)— where N is attached to the carbon bearing the $R_5$ substituent;

$R_6$ is selected from the group consisting of G and $CH_2G$;

G is aryl, wherein said aryl is mono- or polycyclic, and is optionally substituted with one or more substituents selected from the group consisting of hydrogen, halo, CN, $CF_3$, $OR_4$, $CO_2R_4$, $NR_4R_4'$, $CONR_4R_4'$, $CH_2OR_4$, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl; and n is 1.

2. The compound or pharmaceutically acceptable salt thereof according to claim 1, wherein $R_1$ is H or alkyl;

$R_2$ is OH;

$R_5$ is alkyl or substituted alkyl.

3. The compound or pharmaceutically acceptable salt thereof according to claim 2, wherein G is:

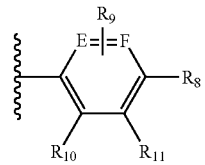

wherein $R_8$, $R_9$, $R_{10}$ and $R_{11}$ are independently selected from the group consisting of H, $NO_2$, CN, $CF_3$, $OR_4$, $CO_2R_4$, $NR_4R_4'$, $CONR_4R_4'$, $CH_2OR_4$, alkyl, substituted alkyl, alkenyl, substituted alkenyl, alkynyl, substituted alkynyl, cycloalkyl, substituted cycloalkyl, arylalkyl, substituted arylalkyl, aryl, substituted aryl, heteroaryl and substituted heteroaryl;

E and F are independently selected from $CR_{12}$;

$R_{12}$ is independently selected from the group consisting of a direct bond and $R_{13}$; and $R_{13}$ is independently selected from the group consisting of H, alkyl, substituted alkyl, alkenyl, substituted alkenyl, arylalkyl, substituted arylalkyl, $CO_2R_4$, $CONR_4R_4'$.

4. The compound or pharmaceutically acceptable salt thereof according to claim 3, wherein $R_8$ is CN.

5. A pharmaceutical composition comprising:

at least one compound according to formula I as defined in claim 1 or a pharmaceutically acceptable salt thereof; and at least one pharmaceutically acceptable diluent or carrier.

6. A compound selected from the group consisting of

2-Chloro-4-((3aR,4R,6aS)-4-hydroxy-1-oxo-hexahydrocyclopentapyrrol-2(1H)-yl)-3-methylbenzonitrile;

2-Chloro-4-((3aR,4R,6aR)-4-hydroxy-1-oxo-hexahydrocyclopentapyrrol-2(1H)-yl)-3-methylbenzonitrile;

2-Chloro-4-((3aR,4R,6aS)-4-hydroxy-1-oxo-hexahydrocyclopentapyrrol-2(1H)-yl)-3-methylbenzonitrile;

2-Chloro-4-((3aR,4R,6aR)-4-hydroxy-1-oxo-hexahydrocyclopentapyrrol-2(1H)-yl)-3-methylbenzonitrile;

2-Chloro-4-((3aR,4R,6aS)-4-hydroxy-1-oxo-hexahydrocyclopentapyrrol-2(1H)-yl)methyl-3-methylbenzonitrile;

2-Chloro-4-((3aR,4R,6aR)-4-hydroxy-1-oxo-hexahydrocyclopentapyrrol-2(1H)-yl)-methyl)-3-methylbenzonitrile;

or a pharmaceutically acceptable salt thereof.

7. A compound according to claim 6 which is
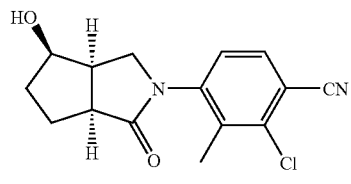
or a pharmaceutically acceptable salt thereof.
* * * * *

UNITED STATES PATENT AND TRADEMARK OFFICE
CERTIFICATE OF CORRECTION

PATENT NO. : 7,696,241 B2
APPLICATION NO. : 11/070025
DATED : April 13, 2010
INVENTOR(S) : James J. Li et al.

Page 1 of 2

It is certified that error appears in the above-identified patent and that said Letters Patent is hereby corrected as shown below:

On the Title Page:

Item (57), ABSTRACT:

Column 2, change " 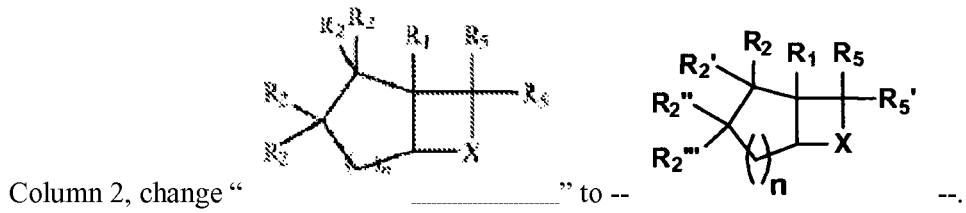 " to -- --.

In the Claims:

Claim 1:

Column 39, lines 13 to 17, change " 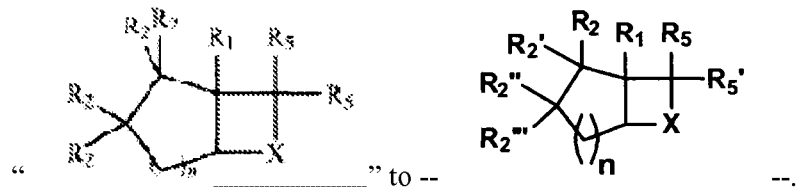 " to -- --.

Column 39, line 67, change "CONR$_4$R$_4$" to -- CONR$_4$R$_4$' --.

Claim 2:

Column 40, line 11, after "OH;", insert -- and --.

Signed and Sealed this
Eighth Day of November, 2011

David J. Kappos
*Director of the United States Patent and Trademark Office*

CERTIFICATE OF CORRECTION (continued)
U.S. Pat. No. 7,696,241 B2

In the Claims;

Claim 6:

Column 40, line 50, after "of", insert -- : --.

Column 40, line 52, change "cyclopentapyrrol" to -- cyclopenta[c]pyrrol --.

Column 40, line 53, change "3aR,4R" to -- 3aS,4S --.

Column 40, line 54, change "cyclopentapyrrol" to -- cyclopenta[c]pyrrol --.

Column 40, line 56, change "4R," to -- 4S, --.

Column 40, line 57, change "cyclopentapyrrol" to -- cyclopenta[c]pyrrol --.

Column 40, line 58, change "3aR,4R" to -- 3aS,4S --.

Column 40, line 59, change "cyclopentapyrrol" to -- cyclopenta[c]pyrrol --.

Column 40, line 60, change "((3aR" to -- (((3aR --.

Column 40, line 61, change "cyclopentapyrrol-2(1H)-yl)methyl" to -- cyclopenta[c]pyrrol-2(1H)-yl)methyl) --.

Column 40, line 63, change "4-((3aR,4R" to -- 4-(((3aS,4S --.

Column 40, line 64, change "cyclopentapyrrol" to -- cyclopenta[c]pyrrol --.